United States Patent [19]

Morris et al.

[11] 4,151,419
[45] Apr. 24, 1979

[54] SOLIDS IRRADIATOR

[75] Inventors: Marvin E. Morris; Jim D. Pierce; Willis J. Whitfield, all of Albuquerque, N. Mex.

[73] Assignee: The United States of America as represented by the United States Department of Energy, Washington, D.C.

[21] Appl. No.: 844,085

[22] Filed: Oct. 20, 1977

[51] Int. Cl.² .................. G01N 21/00; G01N 23/00
[52] U.S. Cl. ................................ 250/453; 250/455
[58] Field of Search .............. 250/492 R, 433, 436, 250/437, 453, 455, 456; 198/862, 854

[56] References Cited

U.S. PATENT DOCUMENTS

| | | | |
|---|---|---|---|
| 3,142,759 | 7/1964 | Jefferson et al. | 250/453 |
| 3,192,054 | 7/1965 | Kuhl et al. | 250/453 |
| 3,396,273 | 8/1968 | Brunner | 250/453 |
| 3,676,675 | 7/1972 | Ransohoff et al. | 250/453 |

Primary Examiner—Bruce C. Anderson
Attorney, Agent, or Firm—Dean E. Carlson; Dudley W. King; Robert Southworth, III

[57] ABSTRACT

A novel facility for irradiation of solids embodying pathogens wherein solids are conveyed through an irradiation chamber in individual containers of an endless conveyor.

6 Claims, 7 Drawing Figures

SOLIDS IRRADIATOR

BACKGROUND OF THE INVENTION

Possible public health hazards have impeded the recycling of sewage sludge as a fertilizer or soil amendment and as an additive to livestock feed. It is desirable to recycle sewage sludge to such beneficial uses because other means of sludge disposal have become increasingly expensive monetarily as well as in terms of energy and ecology.

Pumping liquid sewage or sewage sludge through a radiation chamber to kill or inactivate pathogens may be uncompetitive with conventional sludge treatment because the relatively expensive radiation source is being used in an inefficient manner, irradiating water rather than pathogens. Using a conventional conveyor in the irradiation of dry sewage sludge also leads to size objections and a wasting of radiation as rays could escape through open areas between containers or buckets.

SUMMARY OF THE INVENTION

In order to overcome or minimize the foregoing and various other problems and drawbacks, it is an object of this invention to provide an apparatus for more efficiently irradiating solids embodying pathogens.

It is an object of this invention to provide an apparatus for irradiating solids which are dry.

It is a further object of this invention to provide a apparatus for the irradiaton of solids embodying pathogens so that the solids may be used as a soil amendment, fertilizer or livestock feed.

The invention comprises a radiation shielding concrete structure housing an irradiation chamber, a conveyor having individual containers therealong for conveying pathogen-containing solids into and out of said irradiation chamber, a radiation source within the radiation chamber, and a water filled pool adjacent said chamber for storing said source when not in use.

DESCRIPTION OF DRAWINGS

Other objects and advantages of the invention will be apparent to those skilled in the art from the followng description with reference to the appended claims wherein like numbers denote like parts and wherein.

DESCRIPTION OF A PREFERRED EMBODIMENT

Figure 1:
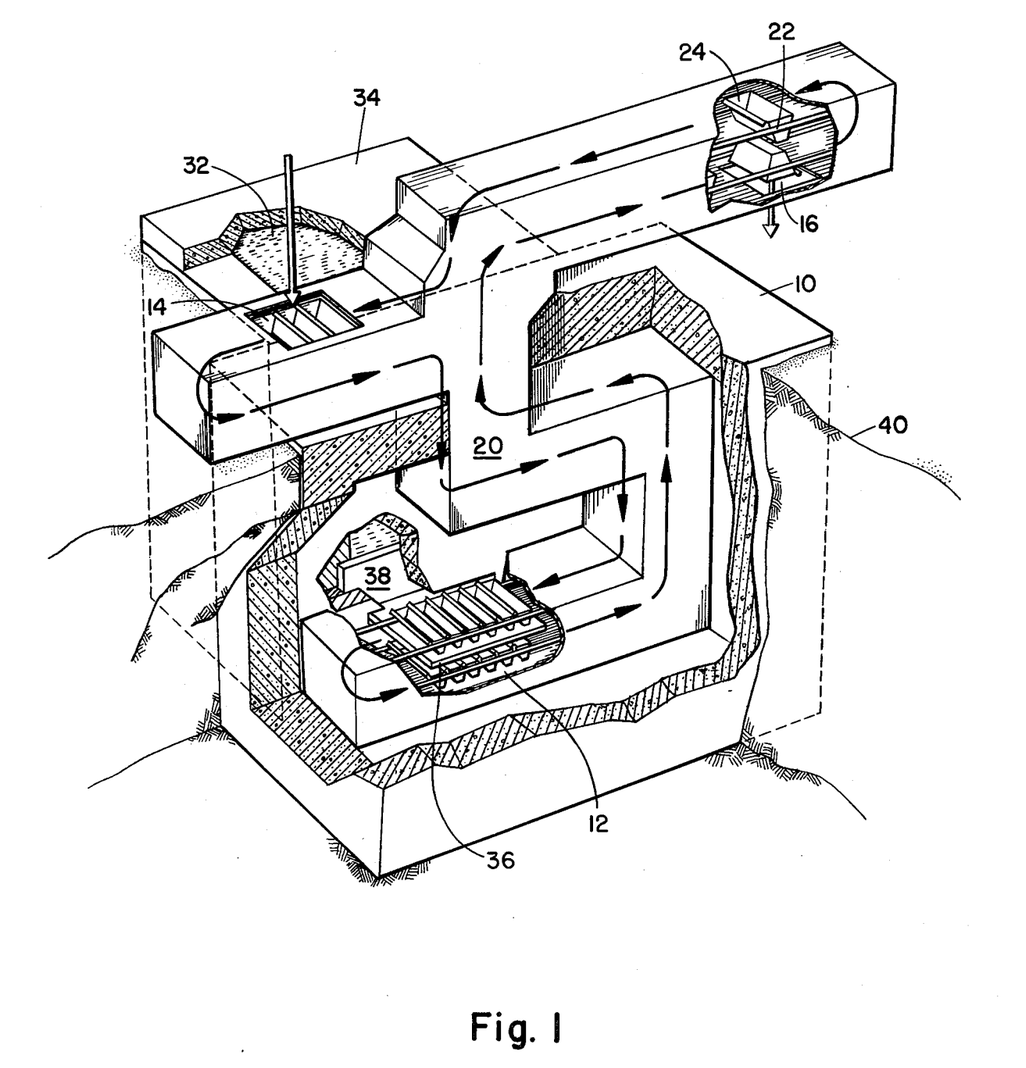
FIG. 1 is a cutaway perspective view of the solids irradiation facility of this invention.

FIG. 1 shows the dry solids irradiation facility in a cutaway perspective view. The general spatial arrangement of the parts of the irradiator are illustrated, such parts comprising; a concrete structure 10, an irradiation chamber 12, a loading area 14, an unloading area 16, a passageway 20, a conveyor 22, a container or bucket 24, a pool 32, a pool lid 34, a radiation source 36, shielding shutter 38, and a ground level 40. The operation and interrelation of these and other parts are described hereinbelow.

Figure 2:
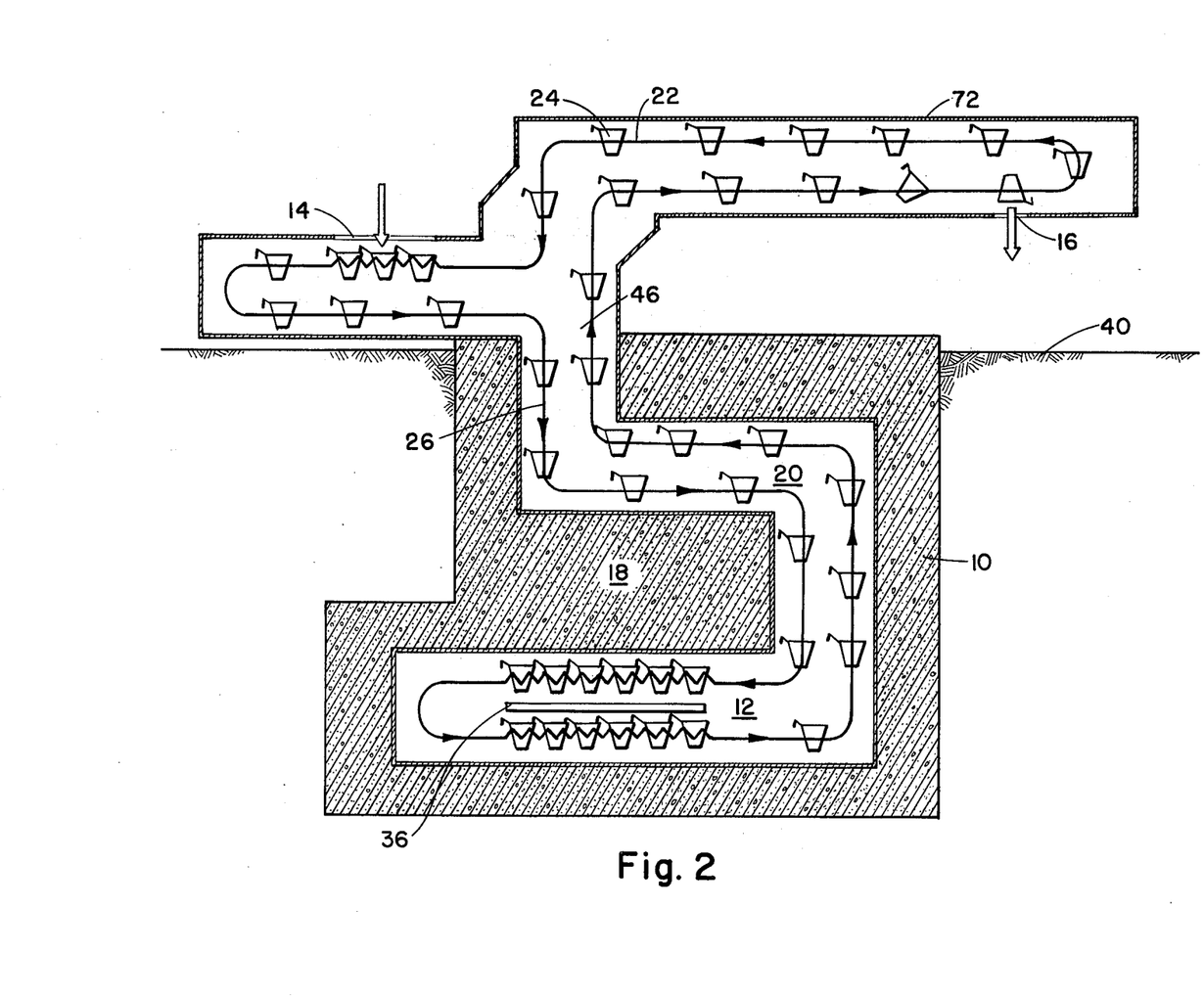
FIG. 2 is a front view of the irradiation facility in cross section.

Referring now to FIG. 2, which is a front view in semi-diagrammatic cross section of the dry solids irradiator, a radiation source 36 is seen to be located within an irradiation chamber 12 enclosed within concrete structure 10.

Figure 7:
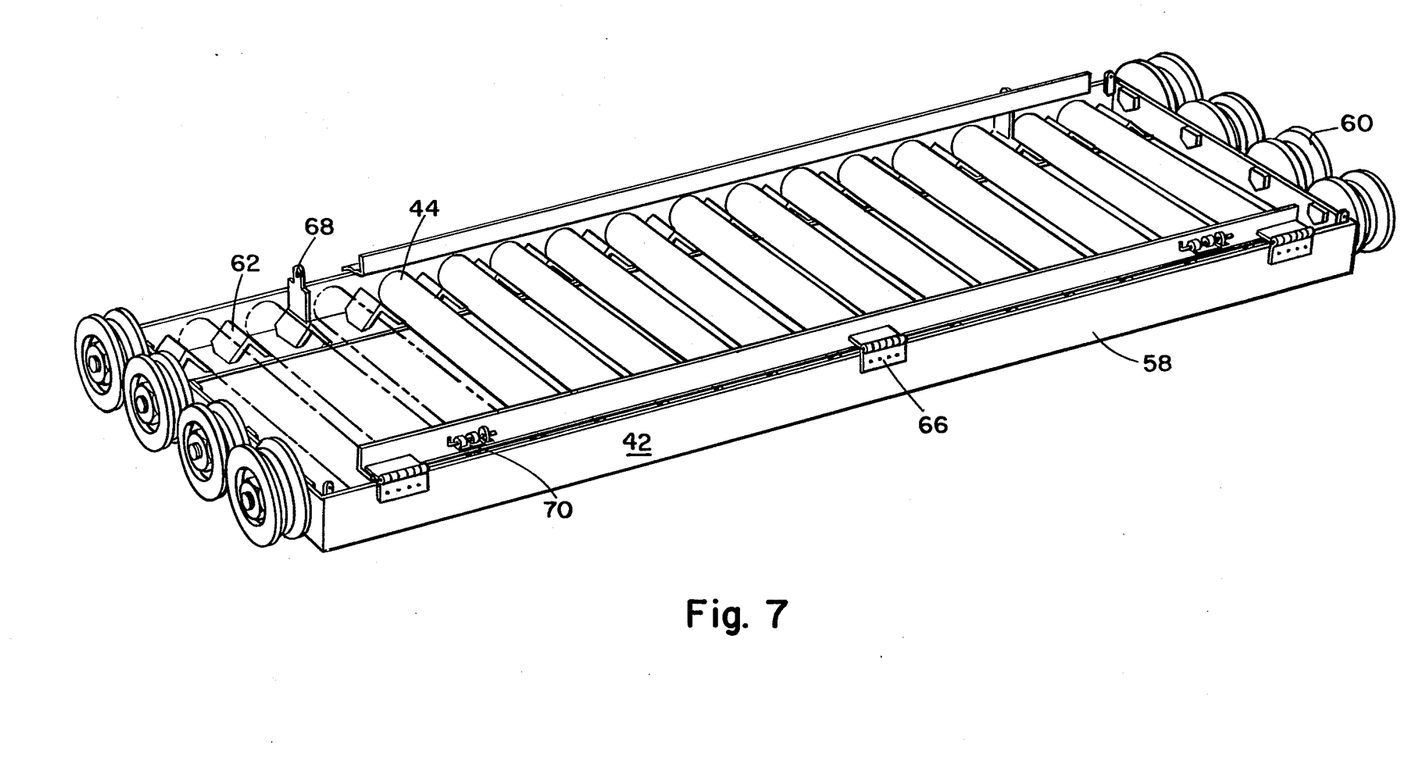
FIG. 7 is an enlarged view of the radiation source plaque.

The radiation source may be in the form of a source plaque 42 comprising about fifteen gamma irradiation pins 44 in a linear array as exemplified in FIG. 7. Each gamma irradiation pin contains about 70 kilocuries of cesium-137 for a total of 1 MCi of Cs-137 in the plaque. This produces a field of 15 kilorads/min of 0.66 Mev gamma radiation within the irradiation chamber. It will be appreciated that this intensity of radiation is sufficient to inactivate pathogens as hereinafter discussed but will not impart objectionable residual radiation to the irradiated solids. Each irradiation pin is a standard WESF (Waste Encapsulation Storage Facility of Hanford, Washington) radioactive waste capsule doubly housing cesium chloride within stainless steel and is approximately 2½ inches in diameter and 24 inches long. A plaque may be 4 inches high, 24 inches wide, and 72 inches long. The source plaque 42 may be constructed of a frame 58 of angle iron having a plurality of wheels 60 mounted on two opposite ends for movement of the source plaque. Within the frame are a plurality of angle iron weldments 62 which define pockets for the placement of the irradiation pins 44. Attached to the frame by appropriate hinges 66 are angle iron retainers 64 which serve to retain the irradiation pins in the pockets. The retainers are secured in place by lugs 68 and locks 70.

Referring back to FIG. 2, the concrete structure 10 preferably allows a radiation exposure to nearby personnel of no greater than 0.01 millirem/hr. This is lower than ERDA Chapter 0524 guidelines by a factor of 60, said guidelines allowing 5 rem whole body exposure per year. This is achieved by first constructing the walls of the structure of up to 5 foot thick concrete. The concrete may be a high strength, low slump concrete made from A Type II portland cement and having at least 4000 psi compressive strength at 28 days and having a maximum slump of 3½ inches. It will be appreciated that a high density concrete, containing, for example, gamma radiation absorbing materials such as manganese, iron or other high z elements, may be used in the structure to either decrease the required thickness of shielding or to increase the degree of radiation protection. Secondly, the concrete structure is located below ground level 40 so as to further attenuate escaping radiation. This also serves to make the facility more resistant to natural disasters such as flood, fire, hurricane, tornadoes and earthquakes as well as more resistant to man-made threats such as accidents, vandalism, and deliberate sabotage.

A passageway 20 is defined by the concrete structure such that the irradiation chamber is communicated with the exterior of the structure. As shown, passageway 20 makes at least three right angle bends to prevent radiation streaming through inlet opening 46. A barrier wall 18 comprised of the same concrete as the rest of the concrete structure lies intermediate the irradiation chamber and the exterior opening to further prevent radiation excape.

An endless conveyor 22 is located partially within the passageway 20 and irradiation zone or chamber 12 and partially without. The conveyor preferably comprises a plurality of individual buckets, carriers, or containers 24 suspended from a pair of roller chains 26. Each container or bucket is free to turn or rotate and is so weighted that it normally remains upright in its travels on the conveyor. Furthermore, each bucket is so spaced apart on the conveyor that the buckets do not interfere with each other on negotiating turns that may be present in the path of the conveyor.

The conveyor may be supported from any suitable framework and supporting sprokets such that it travels an endless path from loading area 14 exterior the concrete structure 10 through the exterior or inlet opening 46 into the passageway 20 and thence into the irradiation chamber 12. The conveyor then travels from the irradiation chamber, again through the passageway, out the exterior opening and to the unloading area 16, from where it returns to the loading area. One such suitable framework is a steel housing 72 which encloses and carries the conveyor in a unitary structure. The conveyor may thus be assembled in a factory and transported as a unit to a remote jobsite to be installed in the concrete structure.

Figure 6:
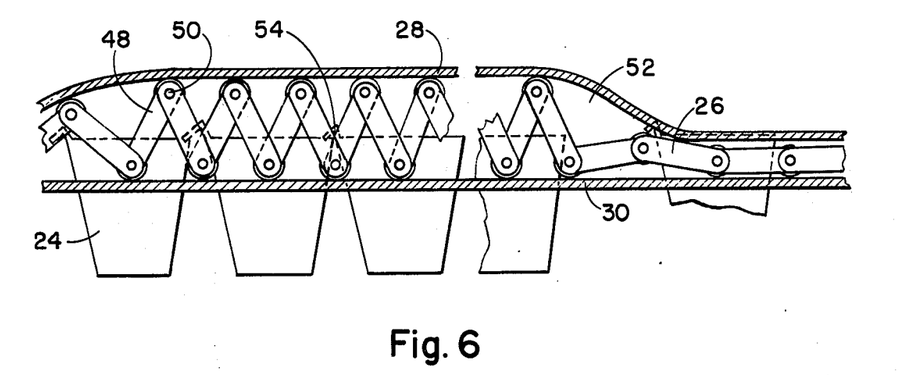
FIG. 6 is an enlarged view of a portion of the endless conveyor.

In the loading area and twice within the irradiation chamber the conveyor performs a movement which may be termed collapsing or folding wherein the container or buckets move from a spaced apart relationship to a closely adjacent or contiguous relationship. One mechanism for accomplishing this collapsing action is illustrated in FIG. 6 which shows a cross section view of a collapsed portion of the conveyor. As shown, the roller chain 26 comprises a plurality of roller chain links 48 and roller chain pins 50. The roller chain pins are constrained to move within a guideway 52 defined by first channel surface 28 and a second channel surface 30. Where the guideway is narrow, the roller chain 26 has a linear configuration, but where the guideway is wider the roller chain adopts a semi-folded configuration. From every fourth roller chain pin 50 is suspended a bucket 24. Where the roller chain adopts the semi-folded configuration, the buckets move adjacent each other in a collapsed position. Appropriate cams and stops may be employed to assist the collapsing action, for example as brought out in U.S. Pat. No. 3,031,066.

The significance of the collapsing action is that it allows more complete source utilization. Ordinarily, clearance must be provided between buckets of a conveyor to allow the conveyor to traverse corners without bucket interference. If a conveyor with such clearance were employed in an irradiator, radiation would pass through the space between the buckets and would thus be wasted.

The ability of the conveyor 22 to negotiate relatively tight turns is further used in this invention, in order to increase source efficiency in that the conveyor may make multiple passes through the irradiation zone. In FIG. 2, two such passes are shown, one above and one below the plane of the source plaque, so as to more efficiently absorb the radiation emanating in those directions—the containers and the materials therein are irradiated from their tops during one pass through the irradiation zone and from their bottoms during another pass. This affords a more uniform irradiation of the material within the containers and thus makes for a more efficient use of the radiation source.

Another advantage of the collapsing conveyor is that spillage may be reduced in loading area 14 by eliminating the clearance between buckets in that area. The buckets may be provided with a lip 54 as illustrated in FIG. 6 to provide an overlap between the buckets in the loading area, thus further reducing spillage.

Referring back to FIG. 2, it is seen that the buckets, being free to rotate, may be inverted in unloading area 16 to discharge any contents. This inversion may be accomplished through appropriate means such as camming surfaces or rack and pinion.

In operation solids are loaded on the conveyor in loading area 14, pass through the irradiation zone 12, and are discharged in unloading area 16.

By solids it is meant any dry or semi-dry material. Material containing up to about 80% moisture would be included in this category, the distinction being whether a material is amendable to standard solids handling techniques such as shoveling as opposed to liquid handling techniques such as pumping through a conduit. The solids irradiator has the capability of irradiating solids in either bulk or packaged form including such things as sewage sludge, foodstuffs, and medical supplies.

The conveyor speed may ordinarily be varied between ½ inch per minute to 4 feet per minute, thus exposing the solids to an accumulated radiation dose of from 6 megarads to 8 kilorads. A conveyor speed of 3 inches per minute will produce the designed dose of 1 megarad. Of course this exposure may be further increased by further slowing of the conveyor, increasing the strength of the radiation source, or passing the solids through the irradiation zone several times. Likewise the exposure may be decreased by increasing the speed of the conveyor or decreasing the strength of the radiation source.

Figure 3:
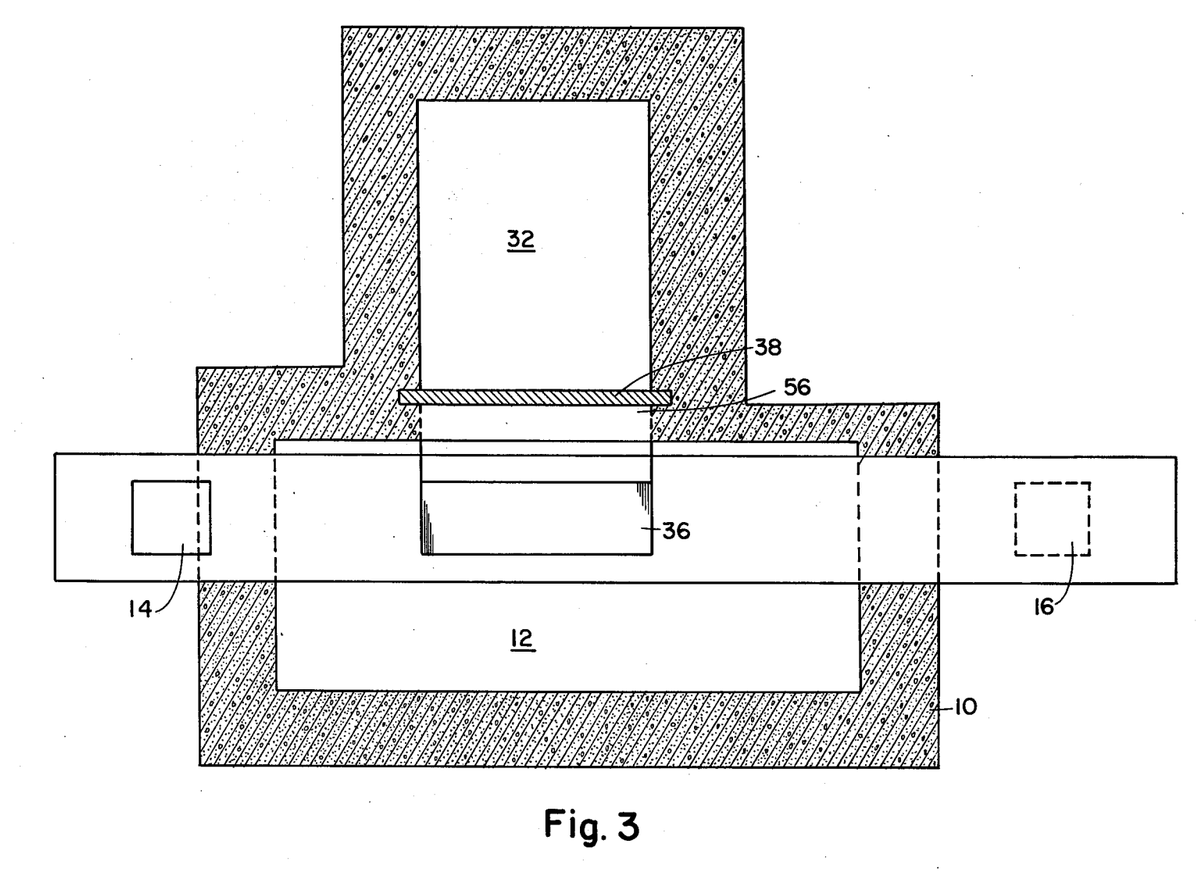
FIG. 3 is a top view of a cross section of the irradiation facility.

Reference is now made to FIG. 3, which is a plan view in cross section of the irradiation facility. This illustrates the general spatial relationship between the concrete structure 10, the irradiation chamber 12, the conveyor 22 with loading area 14 and unloading area 16, and the radiation source 36.

Adjacent and in communication with the irradiation chamber 12 is shown a water pool 32. Between the pool and chamber is a shielding shutter 38. This shutter or door weighing 2½ tons is about 9 inch thick lead encased in steel and is capable of preventing significant penetration of the gamma rays emanating from the source. The shutter is movable and is normally interposed between the water pool and the irradiation chamber. If, for example, it is necessary for personnel to enter the irradiation chamber to perform maintenance upon the conveyor, the radiation source would be removed from its position in the irradiation chamber through a suitable gallery or delivery port 56 to a position in the water pool, and the lead shutter would be positioned intermediate the water pool and the irradiation chamber. By this means, the radiation level in the irradiation chamber is reduced sufficiently such that personnel may enter the chamber for whatever period is necessary to make whatever repairs that might be required.

Figure 4:
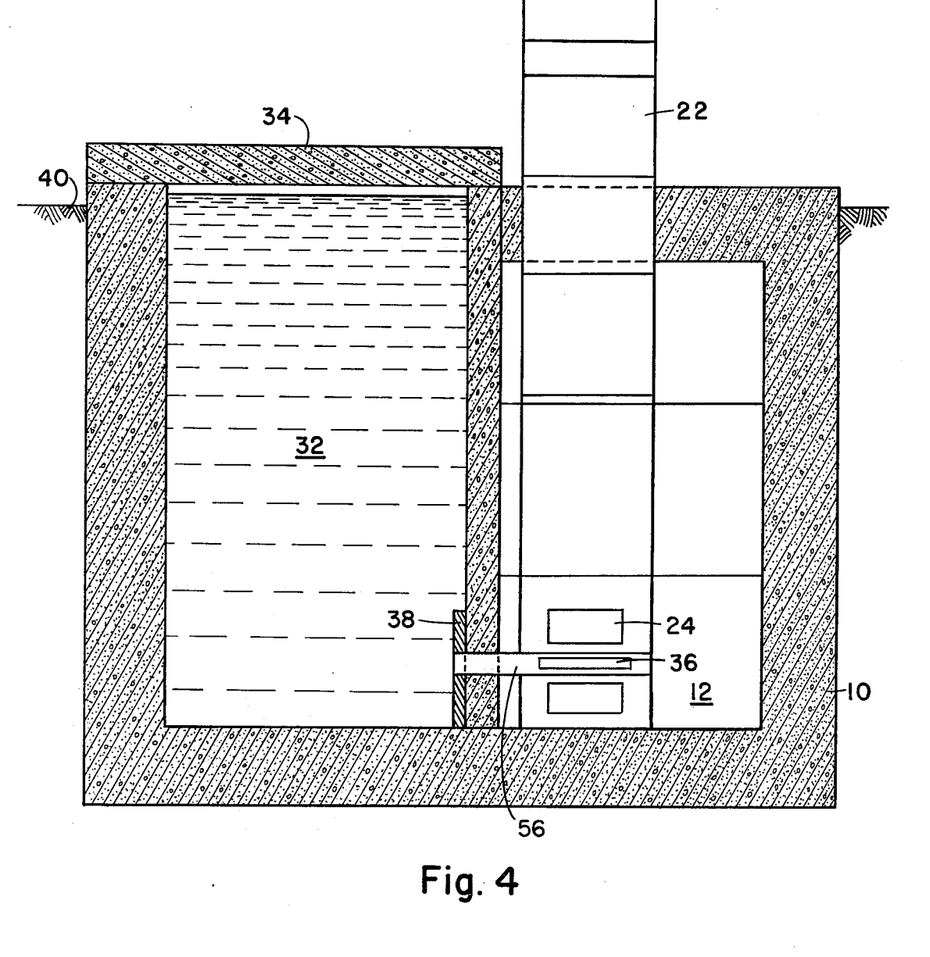
FIG. 4 is an end view of a cross section of the irradiation facility.

Reference is now made to FIG. 4 which shows in end view a cross section of the solids irradiation facility. Again the spatial configuration is illustrated wherein a concrete structure 10 is situated substantially below ground level 40 and contains irradiation chamber 12 into which extends a portion of conveyor 22. Two containers or buckets 24 comprising said conveyor are shown above and below radiation source 36 which in turn is housed within gallery 56 which communicates between the irradiation chamber and water pool 32.

Shutter 38 is shown generally intermediate the water pool and the irradiation chamber where it may block or allow communication between these two chambers.

Water pool 32 may be constructed of the same concrete that makes up concrete structure 10 and may be a separate structure adjacent to concrete structure 10 or it may conveniently be an integral part of said structure. The water pool may be constructed with 4 feet thick walls and bottom and be lined with stainless steel so as to be leak tight and may be about 8 feet wide, 10 feet long, and 20 feet deep. The top of the pool is closed with a removable cover or lid 34 which may be constructed of 5 feet thick concrete. When it is desired to install, remove, or otherwise work on the source plaque 42 or irradiation pins 44 the pool is filled with water or other radiation absorbing liquid. The cover 34 is then removed from the pool 32 to allow access to the interior of the pool. Using standard techniques and equipment well known in the art, the source plaque or irradiation pins may be manipulated below the surface of the water without danger to personnel. For example, in installing the irradiation pins into the source plaque, a transportation cask containing irradiation pins of the sort used in the industry would be submerged in the pool and unsealed, the pins would be removed from the cask for placement within the source plaque, and then the empty cask would be removed from the pool. A similar operation would be performed for removing or replacing spend or defective irradiation pins. When such operations were complete, the lid would be replaced on top of the pool and the water could be removed.

Figure 5:
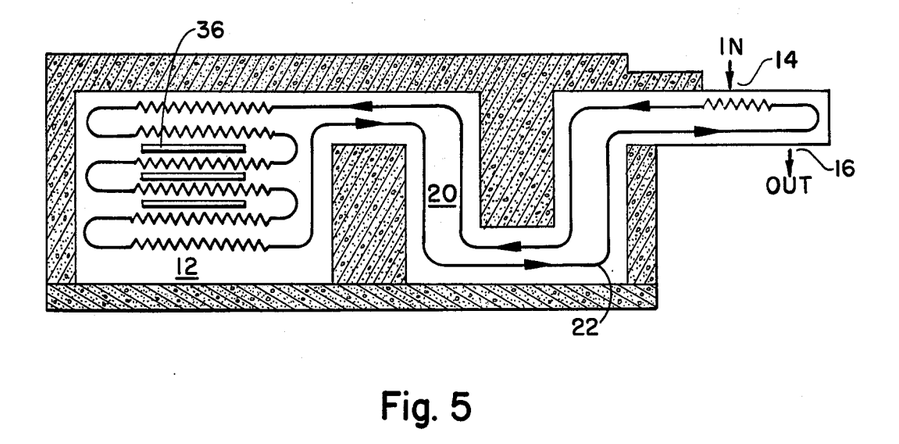
FIG. 5 is a front view of an alternate arrangement of the solids irradiation facility.

Reference is now made to FIG. 5 which illustrates in cross section an alternative arrangement which may be suitable for a larger irradiator. In this arrangement a concrete structure 10 again houses an irradiation chamber 12 which is in communication with the exterior through passageway 20. Conveyor 22 is partially housed within passageway 20, having loading 14 and unloading zones 16 exterior to the concrete structure and making multiple passes through the irradiation chamber. A plurality of radiation sources 36 are located in irradiation chamber 12 and are so spaced that gamma radiation which is not absorbed within one flight of the conveyor has a probability of being absorbed with another. This geometric arrangement allows greater throughput by both increasing the strength of the radiation field and increasing the efficiency of radiation absorbtion. Many other alternative configurations may be suggested to those skilled in the art by the teachings of this invention.

Pathogens are disease causing organisms such as bacteria, viruses, and parasites. It is known that pathogens may survive various sewage treatment processes; it is known that pathogens survive in soil; it is known that pathogens are transmitted to and contaminate vegetable products; and finally it is known that many disease outbreaks by the process suggested by the above facts—pathogenic organisms present in sewage have been deposited in soil, survived to contaminate vegetables, been ingested by humans and caused disease epidemics. Survival times of various disease causing organisms in soil have been reported and is shown in Table I.

TABLE I

SURVIVAL TIMES OF ORGANISMS

| Organism | Media | Survival Time |
|---|---|---|
| *Anthrax bacteria* | In water and sewage | 19 days |
| *Ascaris eggs* | On vegetables | 27–35 days |
| | On irrigated soil | 2–3 days |
| | In soil | 6 years |
| *B. dysentariae flexner* | In water containing humus | 160 days |
| *B. typhosa* | In water | 7–30 days |
| | In soil | 29–58 days |
| | In soil | 60–70 days |
| | On vegetables | 31 days |
| Coliform | On grass | 14 days |
| | On clover leaves | 12–14 days |
| | On clover at 40–60% humidity | 6 days |
| | On lucerne | 34 days |
| | On vegetables (tomatoes) | 35 days |
| | On surface of soil | 38 days |
| | At −17° C. | 46–73 days |
| *Entamoeba histolytica* | On vegetables | 3 days |
| | In water | months |
| Leptospira | In river water | 8 days |
| | In sewage | 30 days |
| | In drainage water | 32 days |
| Liver fluke cysts | In dry hay | few weeks |
| | In improperly dried hay | over a year |
| Poliovirus | In polluted water at 20° C. | 20 days |
| Salmonella | On grass (raw sewage) | 6 weeks+ |
| | On clover (settled sewage) | 12 days |
| | On vegetables | 4 weeks |
| | On vegetables | 7 days |
| | On vegetables | 40 days |
| | On beet leaves | 3 weeks |
| | On grass | Over winter |
| | On surface of soil and potatoes | 40 days+ |
| Salmonella | On carrots | 10 days+ |
| | On cabbage and gooseberries | 5 days+ |
| | In sandy soil - sterlized | 24 weeks |
| | In sandy soil - unsterilized | 5–12 weeks |
| | On surface of soil (raw sewage) | 46 days |
| | In lower layers of soil | 70 days |
| | On surface of soils (stored sewage) | 15–23 days |
| | In air dried, digested sludge | 17 weeks+ |
| *Schistosoma ova* | In digestion tanks | 3 months |
| | In sludge at 60°–75° F. (dry) | 3 weeks |
| | In septic tank | 2–3 weeks |
| Shigella | On grass (raw sewage) | 6 weeks |
| | On vegetables | 7 days |
| Streptococci | In soil | 35–63 days |
| | On surface of soil | 38 days |
| *S. typhi* | In water containing humus | 87–104 days |
| Tubercle bacteria | On grass | 10–14 days |
| | In soil | 6 months+ |
| | In water | 1–3 months |
| *Typhoid bacilli* | In loam and sand | 7–17 days |
| | In muck | 40 days |
| *Vibrio comma* | In river water | 32 days |
| | In sewage | 5 days |

The disposal of sewage sludge has become a national problem. Sewage sludge is the particulate mass formed by gravity separation of sewage and normally contains about 3 to 10% solids. Presently over 5 million dry tons of sewage sludge are produced each year. Table II further illustrates the magnitude of the sludge problem by showing the amount of sludge estimated to be generated in 10 metropolitan areas of the United States.

TABLE II

| City | Quantity of Sludge (Dry Tons/Day) |
|---|---|
| New York (Metro) | 1100 |
| Chicago | 1000 |
| Los Angeles | 900 |
| Philadelphia (Metro) | 340 |
| Detroit | 290 |
| Houston | 290 |
| Baltimore | 250 |
| Dallas | 210 |
| Washington | 720 |
| Cleveland | 360 |

Because of heightened appreciation of ecological and energy considerations, prior art methods of sewage sludge disposal, such as ocean dumping, incineration, landfill, or heat treatment, may be unacceptable or uneconomic.

It has been known for some time that ionizing radiation would inactivate pathogens. It has been found that approximately $10^6$ rads of gamma radiation are sufficient to kill the pathogens in sewage. One radiation source which has been proposed for use in sewage treatment is cobalt-60 with its gamma radiation of 1.22 Mev. Because this isotope must be specially manufactured, it is relatively expensive. A second radiation source that has been suggested is electron bombardment from a linear accelerator. Because of the rising cost of electricity, this mode of radiation is becoming increasingly more expensive. It has been suggested to use the radiation from a reactor or the radiation from the spent fuel rode of a reactor to irradiate sewage. Here problems of reactor licensing or induced readioactivity may be prohibitive.

The use of cesium-137 as a radiation source may obviate many of the above problems. This substance is a fission product which may be obtained during the reprocessing of spent reactor fuel elements. As such, it is ordinarily considered a liability, necessitating expensive long term storage, but through use in the present invention it may become an asset. Furthermore, the 0.66 Mev gamma radiation of cesium-137 is far below the 10 Mev energy required to induce radioactivity in sewage sludge.

Prior art sewage irradiators which comprise flowing either liquid sewage or a liquid sewage sludge past a radiation soruce waste much of their energy irradiating water rather than pathogens. These include the treatment of sewage disclosed by H. R. Spragg in U.S. Pat. No. 3,677,935; the recirclating pumped flow of sewage around a radiation source in a pilot plant in Geiselbullach, Federal Republic of Germany; a conceptual design of General Atomics wherein sewage is pumped past TRIGA reactor rods; a conceptual design of the Metropolitan Sanitary District of Chicago wherein sewage or sludge is flowed through a tank containing a radiation source within a tube bundle; a thermoradiation concept of Sandia Laboratories wherein sewage is heated to 160° F. before it is pumped over a radiation source; and a proposed high energy electron bombardment of a flow of sewage at Boston's Metropolitan Commissioners Deer Island Plant.

As has been pointed out, sewage and sewage sludge consist primarily of water and in the prior art irradiators much of the energy is wasted irradiating water rather than pathogens. It is known that the solids content can be increased to 15% by gravity thickening, to 30% by centrifuging or to 40% by pressure filtration. The process of composting sewage sludge promises to increase the solids content of sewage sludge to 60%. Briefly this process cnsists of mixing sludge with a bulking agent such as wood chips and stacking the material in windrows. The natural action of thermophilic microorganisms raises the temperature of the pile to about 60° C. when many of the pathogens are killed and where water is lost through evaporation. In periods of wet or cold weather, this pathogenic action may be incomplete.

If the process of sludge composting as noted above is combined with sludge irradiation of this patent application a synergism is realized wherein the composting reduces the moisture content of the sludge making for improved source efficiency and the irradiation reduces the amount of time and the amount of land required for the composting step.

Once sewage sludge has been sterilized it becomes an asset rather than a liability. It is estimated that irradiated sewage sludge would have a value of about $60/ton when used as a fertilizer or soil amendment. This use has been known for centuries, particularly in the poorer regions of the world, but it was not known how to economically eliminate public health hazards from this use. When sludge is used as a fertilizer it returns major nutrients to the soil such as nitrogen, phosphorous, potassium, and iron as well as micronutrients and trace elements. When sludge is used as a soil amendment it increases the soils tilth and moisture holding properties.

Another use for irradiated sewage sludge is use as an additive to livestock feed. Sewage sludge may contain nutritive values such as proteins, proteinaceous materials, fats, sugars, and starches as well as nitrogenous materials that may be advantageusly added to animal feed. Use of excreta for its nutritive value is not unknown, as disclosed for example in U.S. Pat. No. 3,919,433 which concern a process for recovering livestock food from cattle excreta. However, the use of human excreta is not ordinarily considered for such use because of the possibility of infecting the livestock with diseases or parasites that are common to both man and animals. It is felt that irradiated sewage sludge would have a value of $100/ton when used as a livestock food additive.

Of course, the dry solids irradiator of this invention may be used to irradiate other solids, particularly where it is desired to irradiate those solids both safely and economically. One large class of solids amenable to radiation treatment is food. For example, the following foods have been studied for radiation treatment: fruits and vegetables such as strawberries, citrus, peaches, pears, cherries, tomatoes, figs, pineapple, papaya, asparagus, nectarines, potatoes, mushrooms, wheat, flour, corn, and onions; fish such as haddock, clams, crab, sole, shrimp and cod; and meats such as poultry, beef, and pork. It should be noted that cold resistant organisms present in frozen food may be killed by irradiation without the need for thawing. Irradiation may reduce spoilage and extend market life without the need for adding chemical preservatives. Irradiation may also be used for pasteurizatin, insect disinfestation, or sprout inhibition of various foodstuffs.

It is noteworthy that prior art food irradiators have primarily been batch-type irradiators, placing a container of food in an irradiation zone for a period of time and then replacing it with another. These irradiators may not possess the source efficiency of the present invention because the solids are not conveyed over and under the radiation source in a collapsing bucket type conveyor.

The various features and advantages of the invention are thought to be clear from the foregoing description. However, various other features and advantages not specifically enumerated will undoubtedly occur to those versed in the art, as likewise will many variations and modifications of the preferred embodiment illustrated, all of which may be achieved without departing from the spirit and scope of the invention as defined by the following claims.

We claim:

1. A facility for gamma irradiation or sterilization of solids embodying pathogens comprising; an underground structure of concrete having an irradiation chamber, an inlet opening above and spaced from said chamber, a barrier portion of concrete intermediate said chamber and inlet opening, and a communicating passageway interconnecting said chamber and inlet opening at an end portion of said barrier and out of direct alignment with said chamber and inlet opening; an endless conveyor carrying individual open top containers along its length extending through said chamber and passageway and inlet opening having a plurality of spaced apart lengths one above the other disposed in said chamber and having an outer portion with upper loading and lower discharging lengths disposed above said concrete structure and irradiation chamber for receiving untreated solids through said open tops and discharging treated solids through said open tops by inverting said containers, said conveyor comprising an endless foldable chain with means for moving said containers into close adjacency disposed in said irradiation chamber and in said upper loading length; a concrete cavity portion at one side of said irradiation chamber for containing a water pool and an irradiation source and having a delivery port adjacent said irradiation chamber, and means for transferring an irradiation source through said port from said cavity portion to an irradiating position in said irradiation chamber adjacent said conveyor and intermediate said upper and lower conveyor lengths to irradiate or sterilize solids carried in said individual containers from their tops during movement in one direction and from their bottoms during movement in an opposite direction.

2. The facility of claim 1 wherein a steel housing encloses and carries said conveyor to thereby provide a unitary structure for mounting in a said concrete structure.

3. The facility of claim 1 wherein the radiation source comprises a rectangular array of about fifteen stainless pins each containing about 70 kilocuries of cesium-137.

4. The facility of claim 1 wherein the concrete structure comprises walls of up to 5 feet thick concrete having a 28 day compressive strength of 4000 psi and a maximum slump of 3½ inches and said walls prevent a radiation field in excess of 0.01 millirem/hr from escaping said facility.

5. The facility of claim 1 wherein the conveyor travels through the irradiation chamber at a speed of from about 0.5 inch per minute to about 50 inches per minute.

6. The facility of claim 1 wherein the solids comprise composted sewage sludge with about 40 to 80 percent water.

* * * * *